US006300070B1

(12) United States Patent
Boles et al.

(10) Patent No.: US 6,300,070 B1
(45) Date of Patent: Oct. 9, 2001

(54) SOLID PHASE METHODS FOR AMPLIFYING MULTIPLE NUCLEIC ACIDS

(75) Inventors: T. Christian Boles, Waltham; Ezra S. Abrams, Newton, both of MA (US)

(73) Assignee: Mosaic Technologies, Inc., Waltham, MA (US)

( * ) Notice: Subject to any disclaimer, the term of this patent is extended or adjusted under 35 U.S.C. 154(b) by 0 days.

(21) Appl. No.: 09/327,083

(22) Filed: Jun. 4, 1999

(51) Int. Cl.$^7$ .............................. C12Q 1/68; C12P 19/34; C07H 21/02; C07H 21/04; C12N 15/00
(52) U.S. Cl. ..................... 435/6; 435/91.2; 536/23.1; 536/24.3; 935/76; 935/77; 935/78
(58) Field of Search ..................... 435/6, 91.2; 536/23.1, 536/24.3; 935/76, 77, 78

(56) References Cited

U.S. PATENT DOCUMENTS

| 4,800,159 | 1/1989 | Mullis et al. | 435/172.3 |
| 5,641,658 | 6/1997 | Adams et al. | 435/91.2 |
| 5,679,773 | 10/1997 | Holmes | 530/334 |

FOREIGN PATENT DOCUMENTS

| WO 94/24312 | 10/1994 | (WO) . |
| WO 98/36094 | 8/1998 | (WO) . |
| WO 98/44151 | 10/1998 | (WO) . |

OTHER PUBLICATIONS

The Stratagene Catalog, p. 39 (1988).*
Chou, Q., et al., "Prevention of pre–PCR mis–priming and primer dimerization improves low–copy–number amplifications", *Nucleic Acids Research*, 20(7):1717–1723 (1992).
Day, Philip, J.R., et al., "Immobilization of polynucleotides on magnetic particles", *Biochem. J.*, 278:735–740 (1991).
Fu, D.J., et al., "Sequencing exons 5 to 8 of the p53 gene by MALDI–TOF mass spectrometry", *Nature Biotechnology*, 16:381–384 (1998).
Laken, S.J., et al., "Genotyping by mass spectrometric analysis of short DNA fragments", *Nature Biotechnology*, 16:1352–1356 (1998).
Horn, T., et al., "Chemical synthesis and characterization of branched oligodeoxyribonucleotides (bDNA) for use as signal amplifiers in nucleic acid quantification assays", *Nucleic Acids Research*, 25(23):4842–4849 (1997).
Ulf Landegren, "The challengers to PCR: a proliferation of chain reactions", *Current Opinion in Biotechnology*, 7:95–97 (1996).
Olejnik, J., et al.,"Photocleavable aminotag phosphoramidites for 5'–termini DNA/RNA labeling", *Nucleic Acids Research*, 26(15):3572–3576 (1998).
Singh, R., et al., "Reagents for Rapid Reduction of Disulfide Bonds", *Methods in Enzymology*, 251:167–173 (1995).
Wang, D.G., et al., "Large–scale Identification, Mapping, and Genotyping of Single–Nucleotide Polymorphisms in the Human Genome", *Science*, 280:1077–1082 (1998).
Rehman, F.N., et al., "Immobilization of acrylamide–modified oligonucleotides by co–polymerization", *Nucleic Acids Research*, 27(2):649–655 (1999).
Horn, T., et al., "An Improved divergent synthesis of comb–type branched oligodeoxyribonucleotides (bDNA) containing multiple secondary sequences", *Nucleic Acids Research*, 25(23):4835–4841 (1997).
Abrams, E.S., et al., "Bridge Amplification for DNA–based Diagnostics", *Diagnostic Gene Detection & Quantification Technologies for Infectious Agents & Human Genetic Diseases*, Ch. 1.9:171–189 (1997).
Bing, D.H., et al., Bridge Amplification: "A Solid Phase PCR System for the Amplification and Detection of Allelic Differences in Single Copy Genes", *Proceedings of the Seventh International Symposium on Human Identification*, Promega Corporation 1996–1998, Madison, WI.

* cited by examiner

*Primary Examiner*—Ethan Whisenant
(74) *Attorney, Agent, or Firm*—Hamilton, Brook, Smith & Reynolds, P.C.

(57) ABSTRACT

A multi-stage bridge amplification method which uses a recovered single-stranded amplification single-stranded nucleic acid molecule to initiate second and subsequent stages of bridge amplification is described.

32 Claims, 9 Drawing Sheets

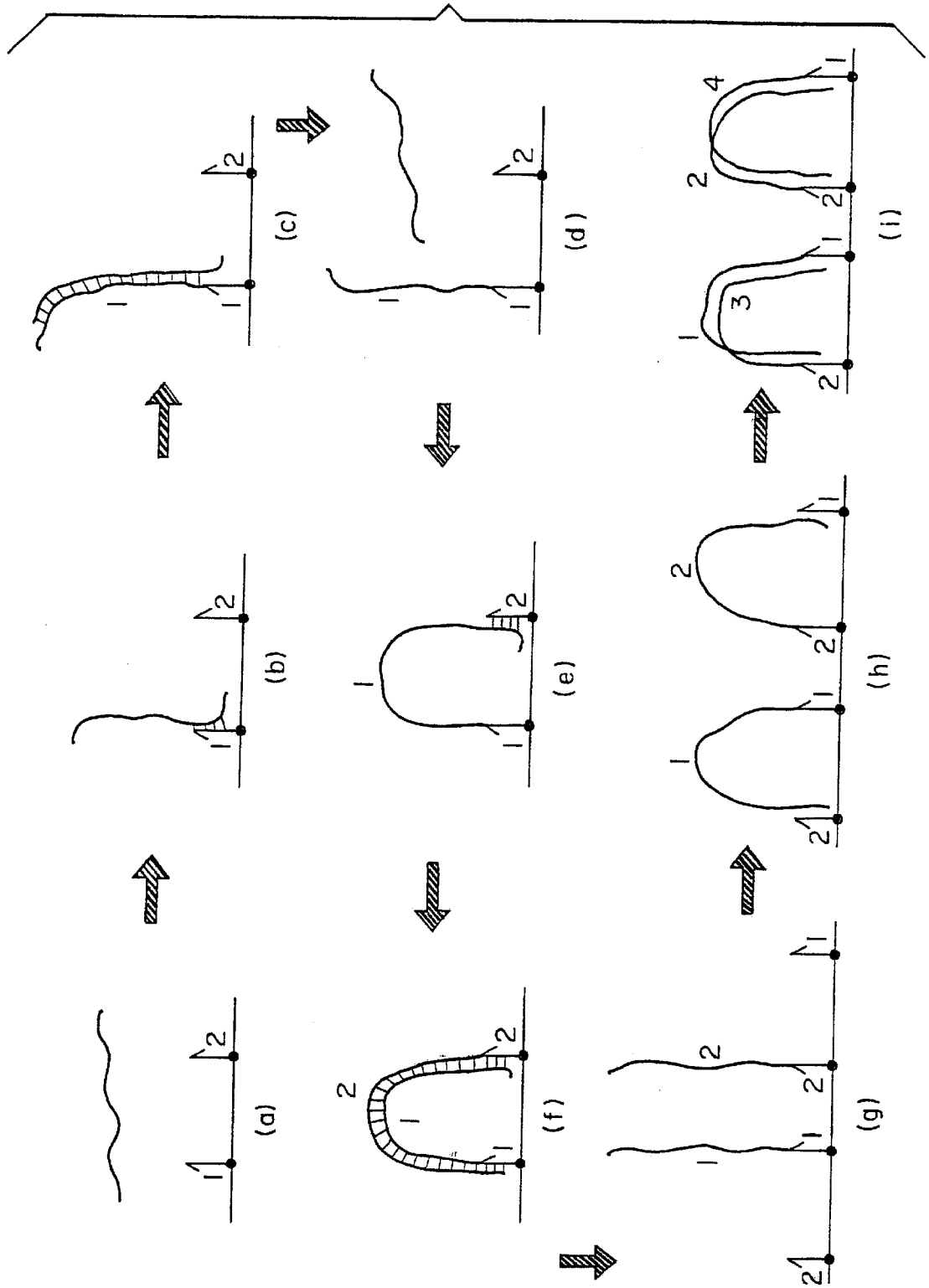

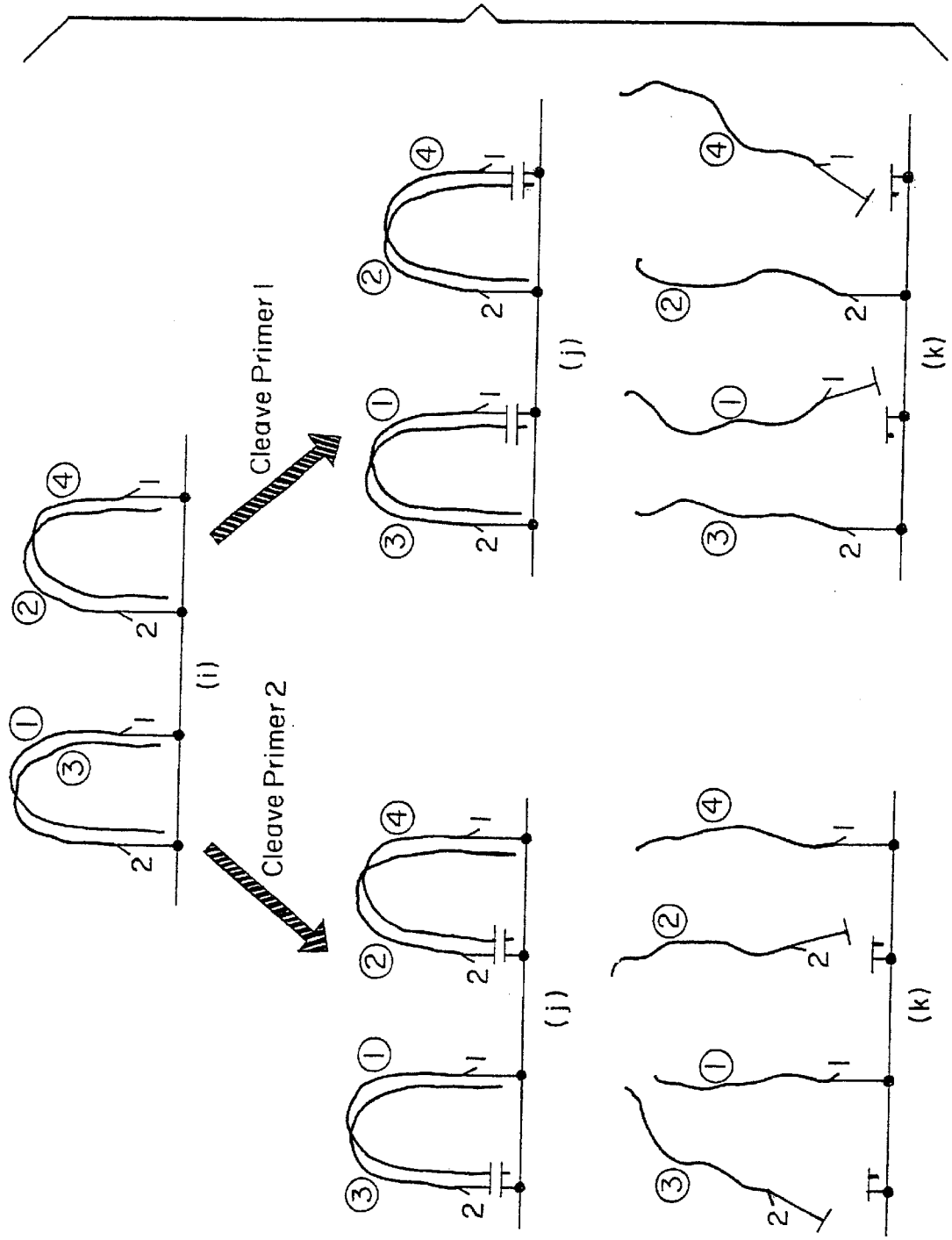

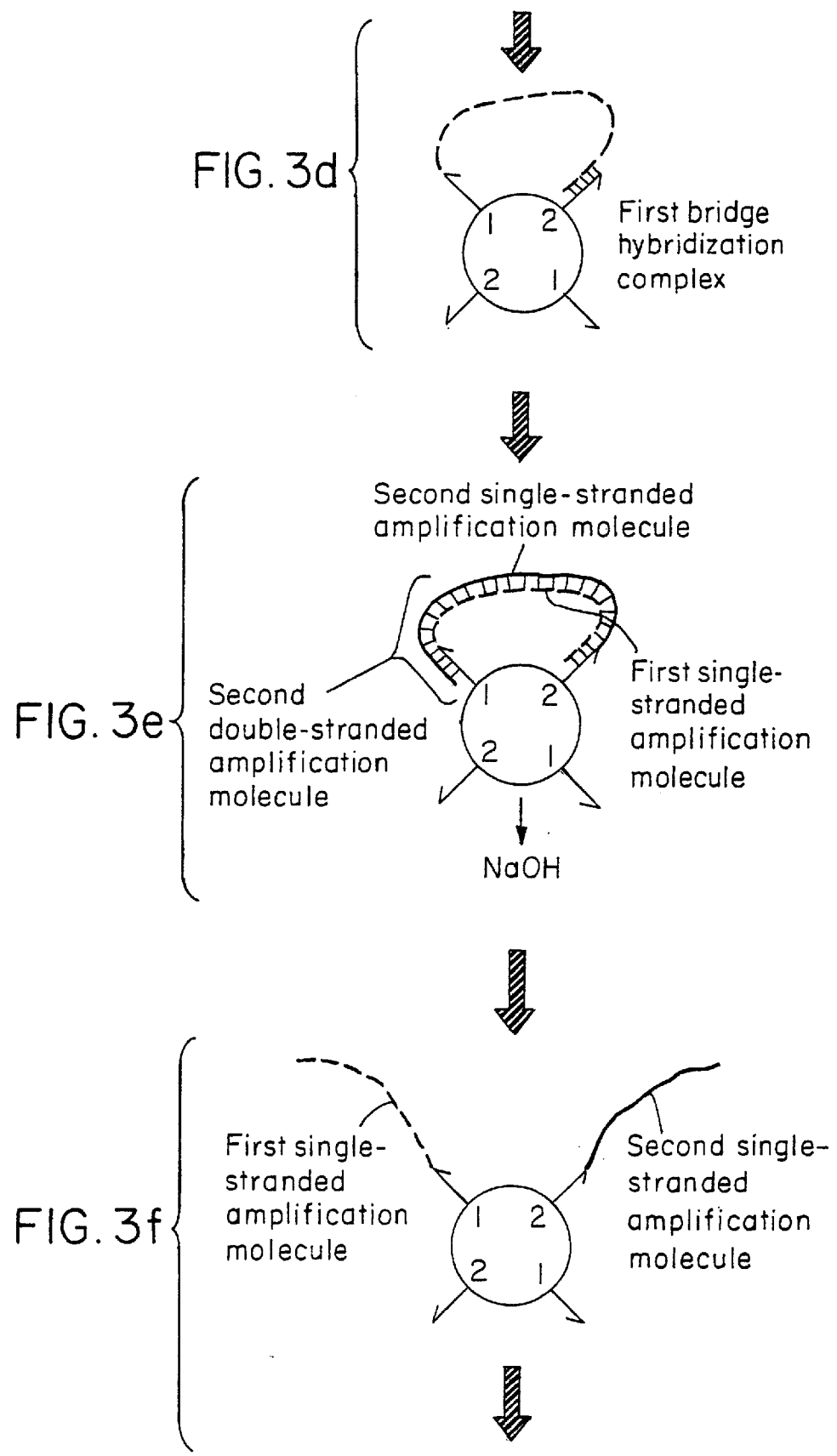

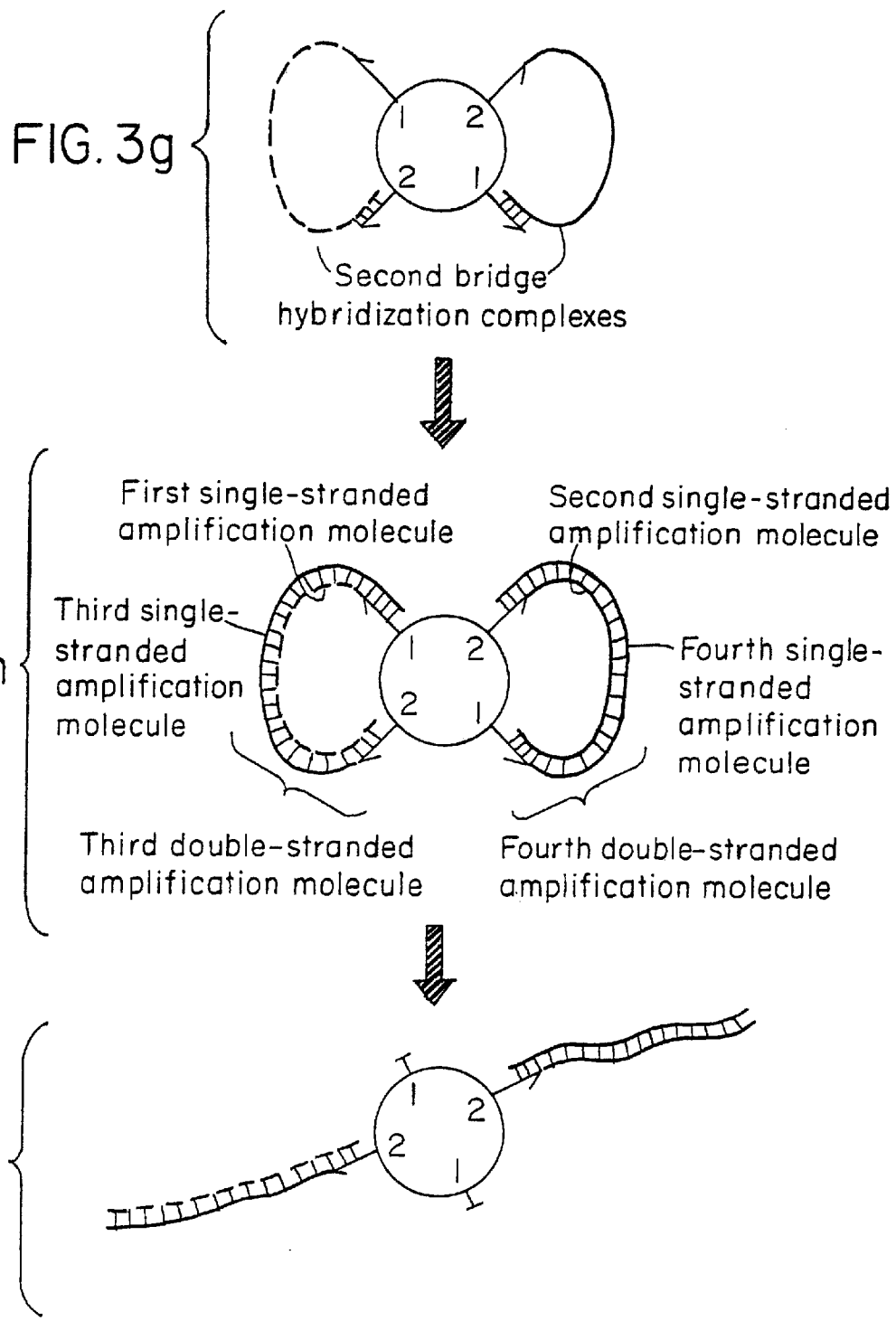

```
gcagaaccgt ggcatggttc gtacaaacca aatgcggtgt tcttgtctgg
------------------> RsaI
Leu2f2 primer caaagaggcc aaggacgcag atggcaacaa acccaaggaa cctgggataa cggaggcttc atcggagatg atatcaccaa acatgttgct ggtgattata ataccattta ggtgggttgg gttcttaact aggatcatgg cggcagaatc aatcaattga tgttgaacct tcaatgtagg gaattcgttc ttgatggttt
cctccacag                          EcoRI     <---------
---------
Leu2R3 primer
```

FIG.4

SEQUENCE LISTING

<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: primer

<400> SEQUENCE: 1
tttttttttc tgcagaaccg tggcatggtt c                              31

```
<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2 ttttttttc tcgagctgtg gaggaaacca tcaag                            35

<210> SEQ ID NO 3
<211> LENGTH: 259
<212> TYPE: DNA
<213> ORGANISM: unknown
<220> FEATURE:
<223> OTHER INFORMATION: Yeast Gene

<400> SEQUENCE: 3
gcagaaccgt ggcatggttc gtacaaacca aatgcggtgt tcttgtctgg caaagaggcc    60
aaggacgcag atggcaacaa acccaaggaa cctgggataa cggaggcttc atcggagatg   120
atatcaccaa acatgttgct ggtgattata ataccattta ggtgggttgg gttcttaact   180
aggatcatgg cggcagaatc aatcaattga tgttgaacct tcaatgtagg gaattcgttc   240
ttgatggttt cctccacag                                               259
```

SOLID PHASE METHODS FOR AMPLIFYING MULTIPLE NUCLEIC ACIDS

BACKGROUND OF THE INVENTION

Recent developments in microarray technology have made it possible to contemplate simultaneously analyzing many hundreds of thousands of individual genetic elements within a single nucleic acid sample. There already exists technology in which probe arrays containing several hundred thousand oligonucleotides are present on a single glass chip (1 cm$^2$). (Wang, D. G., et al., *Science*, 280:1077–1082 (1998)). However, this increase in synthesis capability has exceeded the capacity of polymerase chain reaction (PCR) amplification technology to provide hybridization targets. For example, a microarray containing probes for 10$^4$ randomly distributed human single nucleotide polymorphisms (SNPs) could be used to generate a detailed genomic map of a single individual in a single hybridization experiment. Currently, it is extremely difficult to amplify more than 100 independent loci in a single PCR reaction. (Wang, D. G., et al., *Science*, 280:1077–1082 (1998)). Therefore, using current PCR technology, at least 100 individual PCR reactions, each reaction amplifying 100 distinct loci, must be performed and pooled to take full advantage of a 10$^4$ loci SNP typing chip.

Similar difficulties are anticipated for other multiplex genotyping technologies, such as mass spectrometry. (Hall et al. *Nature Biotechnology*, 16:1352–1365 (1998), and Fu et al., *Nature Biotechnology*, 16:381 (1998)). For this reason, there is a need for new methods that enable massively multiplex nucleic acid amplification. Ideally, such methods would make it possible to produce 10$^3$ to 10$^4$ different products in a single reaction. Coupled with microarray or multiplex mass spectrometry typing methods, such multiplex amplification methods would make it possible to rapidly generate high density, whole genome SNP maps for large numbers of individuals. This would immediately accelerate genetic research in many areas including genetic analysis of complex traits (e.g., asthma, high blood pressure, and various forms of heart disease), human genetic disease research, pharmacogenomics and cancer biology. Improved multiplex amplification methods would also greatly facilitate analysis of gene expression.

SUMMARY OF THE INVENTION

The present invention discloses methods for amplifying target nucleic acid molecules using a solid-phase amplification method. One such method is described in U.S. Pat. No. 5,641,658, the teachings of which are incorporated by reference herein in its entirety. This single-stage solid-phase amplification method is referred to herein as "bridge amplification."

The present invention encompasses a multi-stage bridge amplification method which uses a recovered single-stranded amplification nucleic acid molecule to initiate a second stage of bridge amplification. Subsequent stages of bridge amplification follow where each subsequent stage of bridge amplification is initiated with a single-stranded amplification nucleic acid molecule produced in the previous stage of bridge amplification. This multi-stage method is recursive, and therefore provides for an iterative process whereby a single target molecule can be amplified over a hundred thousand-fold. This iterative process significantly increases the amplification power of bridge amplification.

More specifically, described herein is a solid-phase, multi-stage method for amplifying one, or more, target nucleic acid molecules comprising two or more stages of bridge amplification. In the present method, one or more single-stranded nucleic acid molecules are produced in the first stage of bridge amplification which are used to initiate a second stage of bridge amplification, and single-stranded nucleic acid molecules produced in the second stage of bridge amplification are used to initiate the third stage of bridge amplification, and so forth, through multi-stages of bridge amplification to produce amplified target molecules.

The first stage of bridge amplification involves one, or more, target nucleic acid molecules mixed under conditions of hybridization with a solid support comprising immobilized oligonucleotide primers which are specific for the target molecules. For example, a sample (i.e., test sample) can contain a single type of target molecule and the solid support can comprise a pair of immobilized primers specific for that type of target molecule. Alternatively, the sample can contain multiple target molecules and the solid support will comprise multiple pairs of immobilized primers wherein each pair of primers are specific for one of the target molecules. The target molecules hybridize with their specific immobilized primers. The hybridization complexes that form are then subjected to amplification via thermocycle reactions, thus forming double-stranded amplification nucleic acid molecules. Amplification comprises approximately from about five to about fifty thermocycles, each thermocycle comprising denaturation, primer annealing and polymerization reactions (primer extension) carried out under conditions appropriate for each reaction. Typically, amplification comprises about thirty-five thermocycles.

The double-stranded amplification nucleic acid molecules are cleaved and denatured, thereby releasing single-stranded amplification nucleic acid molecules. These newly released single-stranded amplification nucleic acid molecules are then contacted with a fresh solid support comprising specific immobilized primers and initiate a second stage of bridge amplification. The stages of bridge amplification can be repeated until the desired amplification of the target molecule is achieved. The amplified target nucleic acid molecules can then be analyzed on the solid support, or they can be cleaved from the support for analysis by solution phase or solid phase methods.

The oligonucleotide primers of the present invention are immobilized to a solid support. These primers are specific for a given target nucleic acid molecule. Preferably, the primers are single-stranded DNA molecules. In one embodiment of the invention, a set of primers (e.g., a set of primers comprises a first and a second primer) specific for amplifying a target molecule is immobilized to a solid support. The first primer is complementary to a nucleotide sequence region contained within the target molecule, for example, the 3' terminal end. The second primer is complementary to the 3' terminal end of the complementary nucleic acid strand of the target molecule. There are multiple sets of primers specific for various target molecules attached to the same solid support. Preferably, at least one member of a primer set contains a cleavable moiety. More preferably, the two primers in each primer set have different cleavable moieties. For example, one member of a primer set can comprise a restriction site within its nucleotide sequence.

Preferably, the target molecule is a DNA molecule. Other nucleic acid molecules are within the scope of this invention, for example, RNA. The target nucleic acid molecule (or simply, target or target molecule) can originate from plant or animal tissue. Preferably, the target molecule contains one nucleotide sequence region that can hybridize to a first immobilized primer. The target molecule can be in a double-stranded or single-stranded form. If the presented target molecule is in a double-stranded form, then it is treated so as to render it into a single-stranded form.

The solid support can be beads, particles, sheets, dipsticks, rods, membranes, filters, fibers (e.g., optical and glass), and the like. Preferably, the solid support is a bead. The material composition of the solid support includes, but is not limited to, plastic, nylon, glass, silica, metal, metal alloy, polyacrylamide, polyacrylate, crosslinked-dextran and combinations thereof. Preferably, the solid support is capable of being modified by the attachment of oligonucleotide primers.

Bridge amplification begins with a hybridization complex formed between a target molecule and a first oligonucleotide primer. (See FIG. 1A). Preferably, the target molecule hybridizes to a first primer immobilized to the solid support, under conditions suitable for hybridization, thereby forming a hybridization complex. (See FIG. 1A (a&b)). The first primer is extended by the addition of deoxynucleotides under conditions suitable for polymerization. (See FIG. 1A (c)). The newly formed duplex molecule comprising the target molecule hybridized to its complementary strand is subjected to denaturation, thereby releasing the target molecule from the duplex. The complementary strand remains attached to the solid support via the first primer. (See FIG. 1A (d)).

The single-stranded complementary nucleic acid molecule forms a bridge hybridization complex by contacting a second primer which is immobilized to a solid support. (See FIG. 1A (e)). Preferably, the second primer is immobilized to the same solid support as that to which the first primer is attached. The second primer is extended by the addition of deoxynucleotides under conditions suitable for polymerization. (See FIG. 1A (f)). This newly formed duplex molecule is subjected to denaturation yielding two single-stranded nucleic acid molecules attached to the solid support via their respective oligonucleotide primers. (See FIG. 1A (g)). Each of the single-stranded nucleic acid molecules can form bridge hybridization complexes. (See FIG. 1A (h)). Once a bridge hybridization complex is formed, nascent complementary strands are synthesized under conditions suitable for polymerization. (See FIG. 1A (i)). This process (i.e., the themocycling process of steps "g" to "i" illustrated in FIG. 1A) is repeated from about five to about fifty times. Typically, amplification comprises about thirty-five thermocycles. Following this process, the duplex nucleic acid molecules are subjected to cleavage. (See FIG. 1B (j)). In one embodiment, the first primers are cleaved using, for example, restriction endonucleases. This cleavage will sever the attachment of the duplex nucleic acid molecules from their attachment to the solid support via the first primer. In another embodiment, the second primer undergoes cleavage, thereby severing the attachment of the duplex nucleic acid molecules from their attachment to the solid support via the second primer. Following cleavage the duplex nucleic acid molecule is subjected to denaturation, thereby releasing a single-stranded nucleic acid molecule (see FIG. 1B (k)) that can be recovered and used to initiate a second round of bridge amplification. (See FIG. 2).

In one embodiment of the present invention, the detection of the presence or absence of one or more target molecules in a test sample using the multi-stage bridge amplification method is disclosed. In this embodiment, the amplification molecules can serve as signals to detect the presence or absence of a nucleic acid target in a biological sample, for example, microbial DNA. During the amplification process nascent amplification single-stranded nucleic acid molecules are formed by the incorporation of deoxynucleotides. One or more of these deoxynucleotides can be labeled prior to incorporation into the nascent amplification single-stranded nucleic acid molecules. The detection of labeled nascent amplification single-stranded nucleic acid molecules is indicative of the presence of at least one target molecule in a test sample. Labels other than radioactivity can be employed, such as chemiluminescence, luminescence and fluorescence.

In another embodiment of the present invention, a kit providing reagents for use in a solid-phase, multi-stage method of amplifying one, or more, target nucleic acid molecules comprising two or more stages of bridge amplification is disclosed. In this kit the single-stranded amplification molecules produced in the first stage of bridge amplification initiate a second stage of bridge amplification, and each subsequent stage of bridge amplification is initiated with a single-stranded amplification molecule produced in the previous stage of bridge amplification, wherein one reagent comprises a solid phase support comprising a set of primers specific for one or more target nucleic acid molecules in quantity sufficient for at least two stages of bridge amplification.

Thus, the present invention provides methods for improved solid-phase amplification of target nucleic acid molecules. In particular, the present invention provides improved multiplex amplification methods for nucleic acid analysis.

BRIEF DESCRIPTION OF THE FIGURES

FIGS. 1A and 1B is a schematic illustration of multi-stage bridge amplification.

FIGS. 3a to 3j is a detailed schematic illustration of multi-stage bridge amplification.

FIG. 4 is the nucleotide sequence of the yeast LEU2 gene target, the PstI and XhoI restriction sites engineered into the 5'-terminal nucleotide sequences of the primers are not shown.

DETAILED DESCRIPTION OF THE INVENTION

Figure 2:
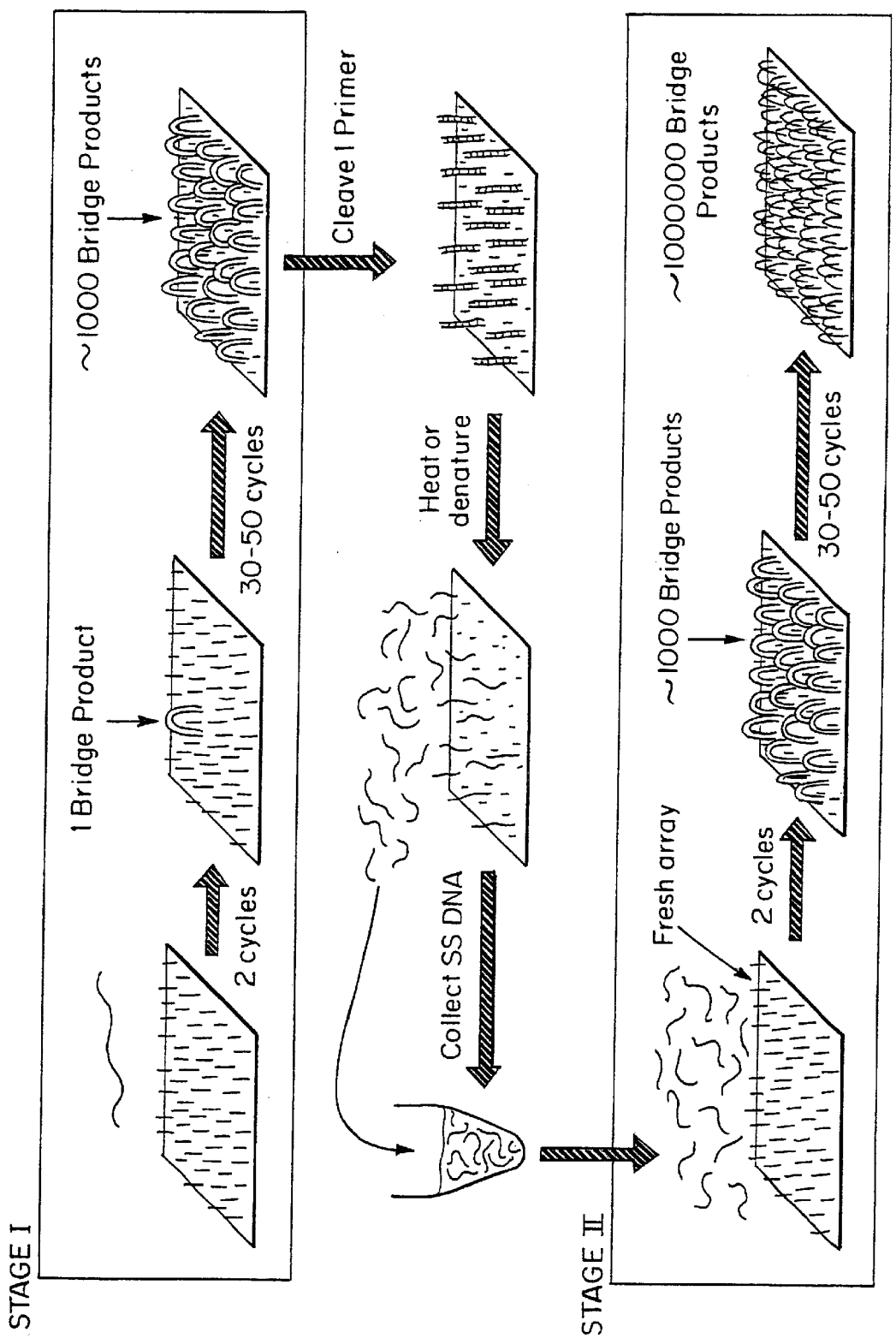
FIG. 2 is a schematic illustration of progress from stage 1 of bridge amplification into stage 2 of bridge amplification.
Figure 3A:
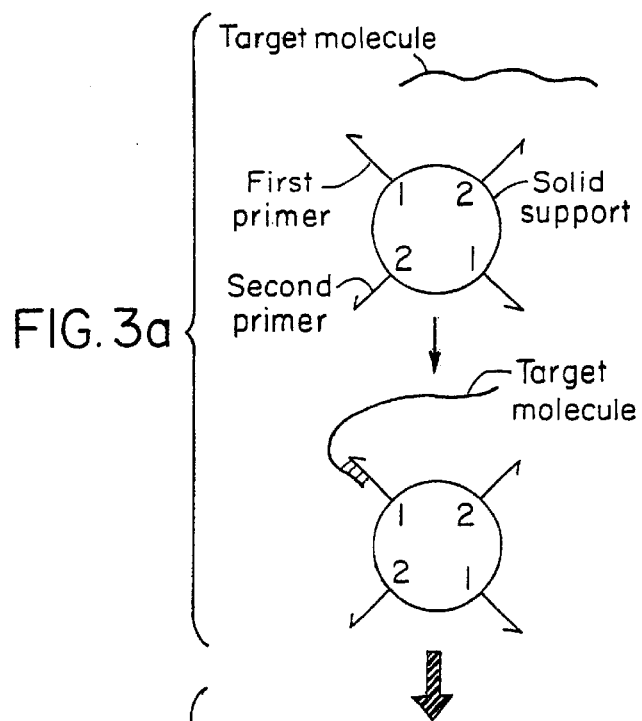
Figure 3B:
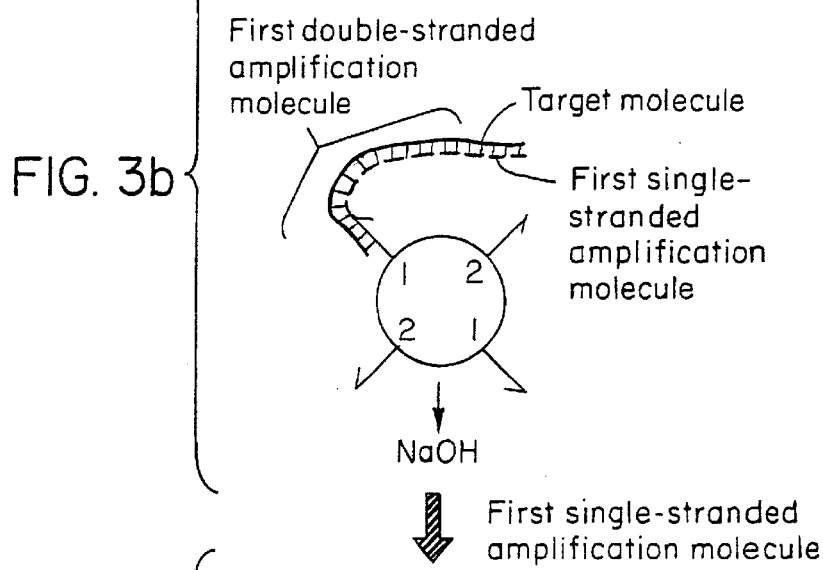
Figure 3C:
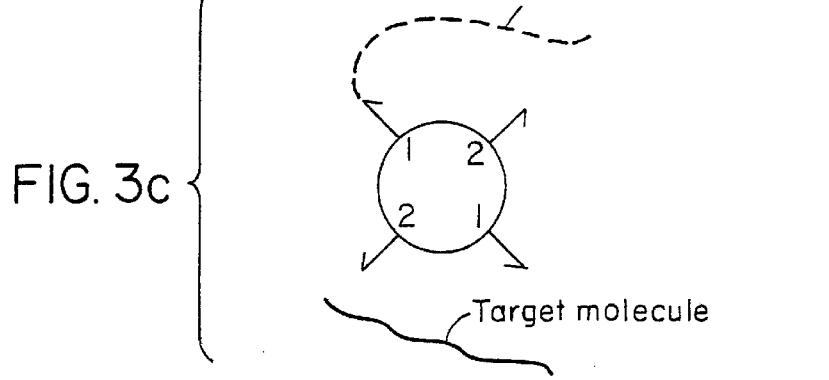
Figure 3J:
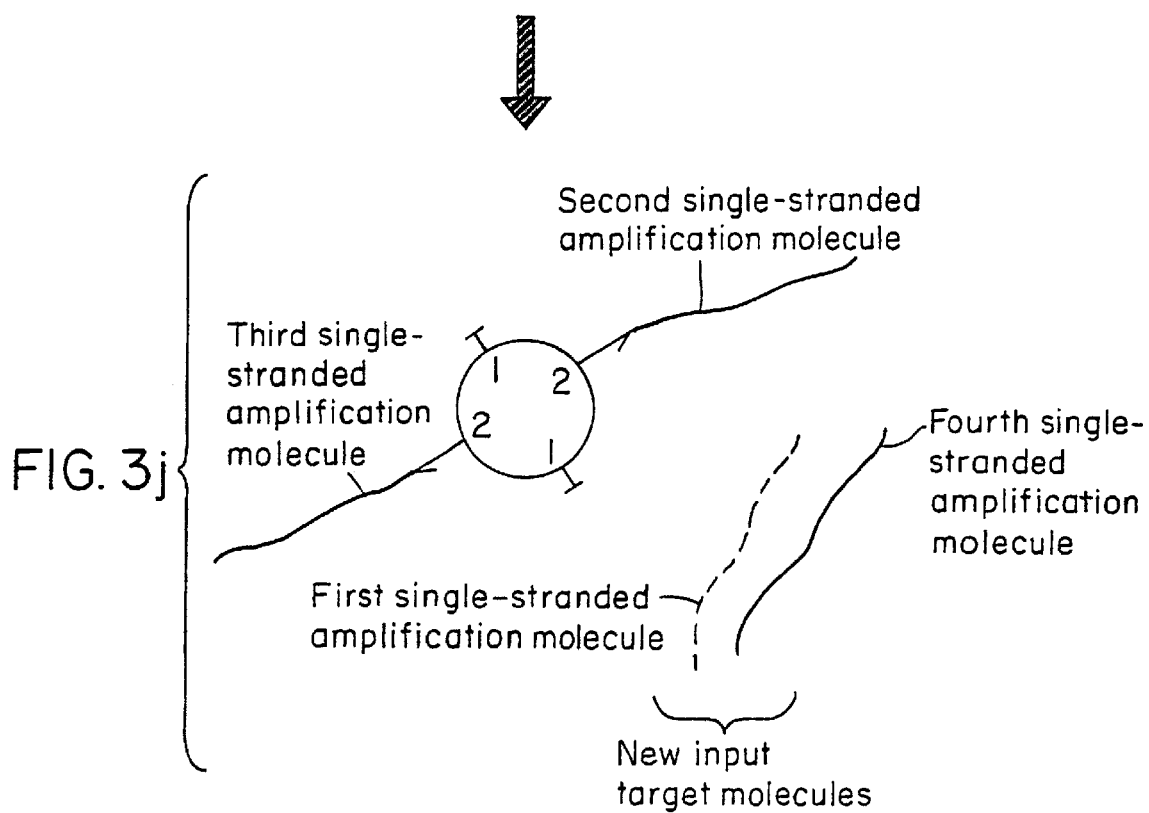

The present invention describes methods for amplifying target nucleic acid molecules using multiple stages of amplification employing a solid support. One such method that employs the use of a solid support is bridge amplification as described in U.S. Pat. No. 5,641,658 to Adams and Kron, the teachings of which are incorporated herein by reference in its entirety. Essentially this methods consists of contacting a target molecule with a solid support to which are attached oligonucleotide primers specific for the target molecule. Hybridization occurs between the target molecule and immobilized oligonucleotide primer. In the presence of appropriate amplification reagents, a complementary single-stranded nucleic acid molecule is synthesized using the target molecule as a template strand for polymerase extension of the immobilized primer to which the target molecule is hybridized forming a duplex amplification product. This duplex is denatured allowing for the target molecule to be released from the duplex. The complementary strand remains bound to the solid support via the immobilized oligonucleotide primer. This complementary strand forms a bridge-like structure by contacting another primer which is complementary to its 3'-terminal end. In the presence of appropriate reagents, a complementary strand is synthesized to the first complementary strand forming a duplex nucleic acid molecule. This duplex is denatured allowing for these complementary strands to contact and hybridize to fresh primers, thus facilitating new rounds of amplification.

Bridge amplification has a significant increase with respect to target capacity when compared to other amplification methods such as PCR. With the present invention, the amplification power using a multi-stage bridge amplification method approaches that of solution phase PCR.

Currently, large numbers of distinct target nucleic acid molecules contained within a single sample can be amplified using bridge amplification. (See U.S. Pat. No. 5,641,658). Other multiplex methods are based upon solution phase PCR and, are limited to approximately 100 target nucleic acid molecules or less in a single reaction. This restriction presumably exists because the PCR primer sets are present at high concentrations and form unproductive "primer-dimer" products that are amplified more efficiently than the authentic amplification targets. (Chou et al., *Nucleic Acid Res.*, 20:1717–1723 (1996), and Landegren, *Current Opinion in Biotech.*, 7:95–97 (1996)). The bridge amplification method obviates this restriction by using primer sets in which both primers for a particular target are immobilized to a common solid support. Unproductive primer-primer interactions are eliminated by primer immobilization. Moreover, amplification of each different target nucleic acid molecule occurs independently in a spatially delineated fashion. Spatial delineation occurs as a result of primer immobilization to any type of solid support. The primary function of immobilization is to eliminate unproductive interactions between primers. Since immobilization to virtually any kind of surface (even beads) reduces the diffusion constant of primers significantly, it is not necessary to use ordered arrays to achieve the benefits of bridge amplification.

Despite the successes of bridge amplification, the method is not suitable for all applications requiring amplification technology. The success of PCR is due to the fact that it easily provides a million-fold amplification of a target nucleic acid molecule. This extent of amplification provides enough product for easy detection using inexpensive and safe fluorescence technologies. Single-stage bridge amplification as described by Adams and Kron (U.S. Pat. No. 5,641,658), however, currently achieves approximately a several thousand-fold target amplification. Thus, single-copy human genes can only be detected in bridge amplification experiments if radioactivity is being employed as the detectable label.

Specifically encompassed in the present invention are methods for amplifying one, or more, target nucleic acid molecules using a multi-stage amplification strategy employing a solid support. The solid support comprises immobilized oligonucleotide primers. In each stage of bridge amplification, single target molecules are amplified several thousand-fold by generating double-stranded amplification nucleic acid molecules (also referred to herein as "double-stranded amplification molecules") which, following denaturation, hybridize with fresh immobilized primers (i.e., unused and unreactive primers) that are in the immediate vicinity of the original primer and are extended by a polymerase to generate new amplification products. One, or more, double-stranded amplification molecules are formed under suitable conditions by contacting (e.g., admixing) one, or more, target nucleic acid molecules with primers that are immobilized to a solid support and with amplification reagents (e.g., deoxynucleotides and DNA polymerase), such amplification reagents are well known to those of skill in the art. (Ausubel, F. M., et al., (eds), Current Protocols in Molecular Biology, John Wiley & Sons (Pub.), vol. 2, ch. 15.4 (1991), the teachings of which are incorporated by reference herein in its entirety). (See FIG. 3).

A set of oligonucleotide primers (comprising a first and a second primer) is attached to a solid support. More than one set of primers designed for different target nucleic acid molecules can be attached to the solid support, for simplicity only one set of primers specific for only one target molecule is described herein. Preferably, the attachment of the primers to the solid support is a covalent attachment. The oligonucleotide primers are preferably single-stranded DNA molecules. Preferably, a first primer is complementary to the single-strand of the target molecule used as a template for the amplification reaction forming the first double-stranded amplification nucleic acid molecule, whereas a second primer is complementary to the complementary strand of the target molecule. Both primers can have their 5'-terminal ends attached to the solid support, thus availing their 3'-terminal ends free to participate in the hybridization and primer extension reactions with the appropriate nucleic acid molecules. (U.S. Ser. No. 08/812,105, and Rehman et al., *Nucleic Acid Res.*, 27:649–655 (1999), the teachings of both of which are herein incorporated by reference in their entirety). The surface density of the primers is sufficiently high to allow the double-stranded amplification molecule of the reaction to span between the attached first and second primers in the form of a single or double-stranded nucleic acid bridge.

The oligonucleotide primers are attached to the solid support using covalent interactions. The oligonucleotide primers can have a range of from about 5 to about several hundred nucleotides (e.g., about 500 nucleotides) in length. Preferably, the primers can have a range of from about 5 to about 50 nucleotides in length. Most preferably, the primers can have a range from about 15 to about 30 nucleotides in length. The primers are designed based upon the target nucleic acid molecules desired to be amplified. The primer sets can be synthesized directly on the solid support, such as a bead support, using orthogonal protecting groups such as dimethyltrityl groups or levulinate (see Horn et al., *Nucleic Acid Res.*, 25:4835–4841 (1997); and Horn et al., *Nucleic Acid Res.*, 25:4842–4848 (1997), the teachings of which are incorporated herein by reference in their entirety), and phosphoramidite reagents and supports for performing 5'→3' synthesis (see Glen Research catalog, 1998, Glen Research, Sterling, Va.; and Coassin et al., International Patent Application No. WO 94/24312, the teachings of which are herein incorporated by reference in their entirety). Alternatively, the primers can be synthesized using standard methods and attached to the support postsynthetically. Methods for postsynthetic attachment of oligonucleotide primers are well known to those in the art. (See Rehman et al., *Nucleic Acid Res.*, 27:649–655 (1999), the teachings of which are herein incorporated by reference in its entirety).

Preferably, the oligonucleotide primers are synthesized such that a modified 5'-acrylamide moiety (Acrydite™ phosphoramidite, Mosaic Technologies, Boston, Mass.) is incorporated which will allow the primers to be immobilized within a solid support, for example, a solid support comprising acrylamide. Chemical or photochemical groups subject to cleavage are incorporated into the structure of the linker moieties on the support, or incorporated into one or both primers before immobilization. Additionally, it is possible to introduce cleavable groups during oligonucleotide synthesis in the form of modified phosphoramidites. (Olejnik et al., *Nucleic Acid Res.*, 26:3572–3576 (1998), the teachings of which are herein incorporated by reference in its entirety). The primers are preferably attached to the solid support using covalent interactions. (See Rehman et al., *Nucleic Acid Res.*, 27:649–655 (1999)). However, noncovalent attachment methods can also be practiced with this invention and are well known to those of ordinary skill in the art. (See Cass, T., and Ligler, F. S. (eds), "Immobilized Biomolecules in Analysis: A Practical Approach." 1998. Oxford University Press, Oxford, UK, the entire teachings of which are incorporated herein by reference).

The solid support can be beads, particles, sheets, dipsticks, membranes, filters, fibers (e.g., glass and optical), and the like. Preferably, the solid support is a bead. Suitable material compositions of the solid support includes, but not limited to, plastic, nylon, glass, silica, metal, metal alloy, polyacrylamide, polyacrylates, crosslinked-dextran and combinations thereof. Preferably, the solid support is capable of being modified by the attachment of oligonucleotide primers. The solid support can have any geometric shape. For example, the solid support can approximate a sphere (e.g., a bead). Alternatively, the solid support is planar as a sheet or membrane. The solid support can be magnetic. Preferably, the solid support is thermally stable (e.g., able to withstand temperatures of up to 100° C.) to withstand thermocycling conditions typically used in PCR.

Typically, the target molecule is a DNA molecule. The target molecule can have a range of length of from about 30 to about 50,000 nucleotides in length. The target nucleic acid is either single or double-stranded. If the target molecule is in a double-stranded form, then it is subjected to denaturation resulting in two single-stranded nucleic acids. Both of these single-stranded nucleic acids individually can also be referred to as target molecules. For simplicity, only one strand will be discussed as a template strand that hybridizes to the first primer, thereby initiating the amplification reaction. However, it should be understood that the process is mirrored for the other target single-strand given an appropriate set of primers (i.e., same primers, but different order of interaction) immobilized to a solid support. Other nucleic acid molecules are also within the scope of this invention, for example, RNA. The target nucleic acid molecule (or simply, target or target molecule) can originate from plant or animal tissue, from a cell, tissue or organ culture system. Preferably, the target molecule has been purified prior to subjecting it to amplification. Methods of purifying nucleic acid are well known to those of ordinary skill in the art. (Ausubel, F. M., et al., (eds), *Current Protocols in Molecular Biology,* John Wiley & Sons (Pub.), vol.1, ch. 2 through 4 (1991), the teachings of which are incorporated by reference herein in its entirety). Preferably, the target molecule, specifically the template strand, contains one nucleotide sequence region that can hybridize to a first immobilized primer.

A hybridization complex is formed by contacting (e.g., admixing) the target molecule with a first oligonucleotide primer, under conditions suitable for hybridization. (See U.S. Pat. No. 5,641,658, and U.S. Ser. No. 08/800,840, the teachings of which are herein incorporated by reference in their entirety). A single-stranded target molecule (i.e., the template strand) hybridizes to a first attached oligonucleotide primer. (See FIG. 3a). The first oligonucleotide primer is a primer that has a nucleotide sequence region that is complementary to a nucleotide sequence region contained within the template strand of the target molecule. The complementary region is from about 5 to about 50 nucleotides in length.

A first double-stranded amplification nucleic acid molecule (also referred to herein as "first double-stranded amplification molecule") is formed by contacting (e.g., admixing) the hybridization complex with amplification reagents under conditions suitable for amplification. (See FIG. 3b). Under suitable amplification conditions, a nascent complementary strand is synthesized using the single-stranded target molecule as a template strand. A double-stranded amplification molecule is formed following this amplification reaction and remains bound to the solid support. Conditions suitable for amplification comprise a thermally stable DNA Polymerase, deoxynucleotides, appropriate ionic strength and pH as well as other necessary reagents to facilitate a nucleic acid amplification reaction well known to those of ordinary skill in the art. (Ausubel, F. M., et al., (eds), *Current Protocols in Molecular Biology,* John Wiley & Sons (Pub.), vol.2, ch. 15.4 (1991), the teachings of which are incorporated by reference herein in its entirety). The first primer is extended with deoxynucleotides forming a first single-stranded amplification nucleic acid molecule (also referred to herein as "first single-stranded amplification molecule"). This first single-stranded amplification molecule is complementary to the target template and together they form the first double-stranded amplification molecule.

The first double-stranded amplification molecule is a double-stranded nucleic acid comprising the target molecule hybridized to its complementary strand (i.e., the first single-stranded amplification molecule). Under denaturing conditions, the bound target nucleic acid molecule is separated from its bound complementary strand (i.e., the first single-stranded amplification molecule). (See FIG. 3c). The first single-stranded amplification molecule contacts the surface of the solid support and hybridizes to a complementary second oligonucleotide primer which contains a nucleotide sequence region complementary to the first single-stranded amplification molecule and is attached to the solid support, forming a first bridge hybridization complex. (See FIG. 3d). The complementary region is from about 5 to about 50 nucleotides in length. Preferably, the solid support is the same support to which the first primer is attached.

A second double-stranded amplification nucleic acid molecule (also referred to herein as "second double-stranded amplification molecule") is formed under suitable amplification conditions where a nascent complementary strand is synthesized using the first single-stranded amplification molecule as the template strand. (See FIG. 3e). The second primer is extended with the addition of deoxynucleotides such that a complementary strand to the first single-stranded amplification molecule is formed. This complementary strand is referred to as the second single-stranded amplification nucleic acid molecule (also referred to herein as "second single-stranded amplification molecule"). The nucleotide sequence comprising this second single-stranded amplification molecule is a sequence that is identical to the original target molecule's nucleotide sequence. Hybridized together, the first and second single-stranded amplification molecules form the second double-stranded amplification molecule.

The second double-stranded amplification molecule is subjected to denaturation. Denaturation is effectuated, for example, by placing the second double-stranded amplification molecule in an alkali environment (e.g., 15 mM NaOH). Alternatively, the double-stranded amplification molecule is subjected to melting temperatures which depend upon many factors such as the nucleotide base constituents. Suitable denaturing conditions are well known to those skilled in the art. Following denaturation, the hydrogen bonds between the first and second single-stranded amplification molecules are broken resulting in first and second single-stranded amplification molecules. These single-stranded molecules still remain attached to the solid support via the oligonucleotide primers. The first single-stranded amplification molecule remains attached via the immobilized first primer; whereas, the second single-stranded amplification molecule remains attached via the immobilized second primer. (See FIG. 3f).

Under suitable denaturation/annealing conditions, multiple second bridge hybridization complexes are formed. (See FIG. 3g which illustrates, for simplicity, only two bridge hybridization complexes). For example, the attached first single-stranded amplification molecule contacts a fresh second oligonucleotide primer, which contains a complementary nucleotide sequence region to the 3'-end region of the first single-stranded amplification molecule, thus forming a second bridge hybridization complex. Similarly, the second single-stranded amplification molecule contacts a fresh first oligonucleotide primer which contains a complementary nucleotide sequence region to the 3'-end region of the second single-stranded amplification molecule, thus forming another second bridge hybridization complex. Preferably, the oligonucleotide primers which are contacted by the first and second single-stranded amplification molecules are immobilized on the same solid support to which the single-stranded amplification molecules are attached.

Third and fourth double-stranded amplification nucleic acid molecules (also referred to herein as "third and fourth double-stranded amplification molecules") are formed by contacting the second bridge hybridization complexes with appropriate amplification reagents. (See FIG. 3h). The first and second immobilized primers are extended by the addition of deoxynucleotides. The extension of the second primer uses the first single-standed amplification molecule as a template forming a third single-stranded nucleic acid amplification molecule (also referred to herein as "third single-stranded amplification molecule"). The hybridized first and third single-stranded amplification molecules form a third double-stranded amplification molecule. In a similar manner, the extension of the first primer uses the second single-stranded amplification nucleic acid molecule as a template forming a fourth single-stranded amplification nucleic acid molecule (also referred to herein as "fourth single-stranded amplification molecule"). The hybridized second and fourth single-stranded amplification molecules form a fourth double-stranded amplification molecule. This amplification thermocycle is typically repeated from about five to about fifty cycles generating multiple third and fourth double-stranded amplification molecules. More typically, amplification comprises about thirty-five thermocycles. Each cycle can consist of 95°, 60° and 72° C. for about one minute duration for each temperature point. Such thermocycling conditions are well known to those skilled in the art. Additional rounds of thermocycling give rise to a multitude of additional amplification double-stranded molecules.

Amplification products from the first stage of bridge amplification are released in a single-stranded form and are used to initiate the next stage of bridge amplification. (See FIGS. 3i&j). The third and fourth double-stranded amplification molecules are cleaved from attachment to the solid support. (See FIG. 3i). Preferably, only one primer for each double-stranded amplification molecule is completely cleaved, yielding a "partially released" double-stranded amplification molecule. As defined herein, "partially released" means that the double-stranded amplification molecule after cleavage remains attached to the solid support via the uncleaved primer. Cleavage can be accomplished by either enzymatic or chemical means. Enzymatic cleavage is accomplished by incorporating a specific restriction endonuclease site within the primers attached to the solid support. Most preferably, the restriction site contained within the first primer is different from that restriction site contained within the second primer (e.g., the first primer contains a EcoRi site, while the second primer contains a HindIII site). In one embodiment of the present invention, the first primer is subjected to cleavage. Alternatively, the second primer is subjected to cleavage.

Methods for cleaving the double-stranded amplification molecule from the solid support other than restriction are also well known to those of skill in the art. For example, chemical cleavage is used if one or both of the two primers are attached to the solid support by a chemical linker that contains a chemically labile group. Dithiol linkages are one example of a linking chemistry that is heat stable but easily cleaved by chemical agents such as dithiothreitol (DTT), β-mercaptoethanol, Tris(2-carboxyethyl) phosphine HCl (TCEP) and other disulfide reducing agents. (Day et al., Biochem. J., 278:735–740 (1991); Singh et al., Methods in Enzymology, 251:167–173 (1995), the teachings of which are herein incorporated by reference in its entirety). Alternatively, photochemical cleavage is employed if one or both of the two primers are attached to the solid support by a linkage moiety that is photochemically labile. Photochemical cleavable attachment chemistries for DNA oligonucleotides have been previously described. (Olejnik et al., Nucleic Acid Res., 26:3572–3576 (1998) and U.S. Pat. No. 5,679,773, the teachings of which are incorporated by reference herein in their entirety). For example, the photochemically cleavable linker can comprise a substituted nitrophenol group.

The cleaved double-stranded amplification molecules are now subjected to denaturation, thereby releasing single-stranded nucleic acid molecules from their double-stranded amplification molecule parent (i.e., the hybridization complex formed between the first and third single-stranded amplification molecules, and between the second and fourth single-stranded amplification molecules). The released single-stranded nucleic acid molecules are recovered and applied to fresh amplification supports to initialize a second stage of bridge amplification. (See FIG. 3j). Subsequent stages of bridge amplification are initiated using single-stranded amplification molecules produced in the previous stage of bridge amplification.

Stages of bridge amplification can be repeated until a desired level of target molecule amplification is achieved. For example, two stages of bridge amplification can yield an amplification on the order of $10^6$-fold (overall for two stages combined, 1000×1000; each stage producing about 1000-fold amplification). If a higher level of amplification is desired, then more stages of bridge amplification can be performed.

Once the desired level of amplification has been achieved, the product formed on the solid support can be analyzed while still attached to the solid support. For example, if the solid support is a bead, the beads can be concentrated and analyzed for signal emission (such as fluorescence). Alternatively, the products can be cleaved from the support and analyzed by solution phase methods, for example, gel electrophoresis. (See the Exemplification).

Denaturation of the cleaved double-stranded amplification molecule is accomplished by exposing the solid support apparatus (i.e., the amplification solid support with attached products) to denaturing conditions, such as high temperatures from about 90° to about 100° C., high pH around 12, or denaturing chemical treatments using organic solvents or chaotropic agents. Alternatively, strand separation is achieved by enzymatic strand-separating methods, for example, treatment of the solid support apparatus with DNA helicases in the presence of ATP. (Lohman, T. M., and Bjornson, K. P., *Annu. Rev. Biochem.*, 65:169–214 (1996), the entire teachings of which are herein incorporated by reference).

Double-stranded amplification molecules can be detectably labeled during the polymerization reaction, for example, using labeled deoxynucleotides incorporated during the amplification process. The label can be radioactive, chemiluminescent, luminescent and fluorescent agents. Preferably, the label is a fluorescent agent. Direct labeling of the nucleic acid molecule of interest using modified nucleotides is accomplished by a number of enzymatic methods well known to those of ordinary skill in the art. (See Sambrook, et al., *Molecular Cloning: A Laboratory Manual*, $2^{nd}$ edition, Cold Spring Harbor Press, Cold Spring Harbor, N.Y. (1989), the teachings of which are incorporated by reference herein in its entirety). To detect a double-stranded amplification molecule, an intercalating dye, such as ethidium bromide, can be used. Detection of a double-stranded amplification molecule can also be accomplished by employing a labeled nucleic acid comprising a nucleotide sequence region which is complementary to a nucleotide sequence region of the double-stranded amplification molecule which hybridizes to that molecule, for example, the third and/or fourth single-stranded amplification molecule.

In one embodiment of the present invention, a method for detecting the presence or absence of a target molecule in a test sample using the multi-stage bridge amplification method is described herein. Amplification products are formed during the amplification stages of the multi-staged bridge amplification method. The products can be labeled and detected as described in the preceding paragraph. (See above and Exemplification). Given the significant increase in amplification power, labels other than radioactivity can be used. Other labels which may be employed in this detection scheme include chemiluminescence, luminescence and fluorescence. Preferably, the label is a fluorescent agent.

In another embodiment of the instant invention, a kit for use in a solid-phase, multi-stage method of amplifying one, or more, target nucleic acid molecules comprising two or more stages of bridge amplification is described. The single-stranded amplification molecules produced in the first stage of bridge amplification initiates a second stage of bridge amplification, and each subsequent stage of bridge amplification is initiated with a single-stranded amplification molecule produced in the previous stage of bridge amplification. One kit reagent comprises solid supports for performing at least two stages of bridge amplification. The solid supports comprise at least one primer set for amplifying one or more target molecules. For example, in one embodiment, the solid support reagent of the kit comprises beads wherein each bead comprises a set of primers specific for one or more target molecules.

The amplification power of solid-phase using this improved method of multi-stage bridge amplification described herein is significantly increased compared to single-stage bridge amplification. Each stage of amplification comprising from about 30 to about 40 amplification cycles can provide a several thousand-fold target amplification. The total extent of amplification over all of the stages is as high as the product of the individual amplification factors from each stage. For example, assuming a 1,000-fold amplification for a single stage of bridge amplification requiring thirty-five thermocycles, three consecutive stages of bridge amplification could yield an overall amplification as high as $10^9$ (assuming perfect recovery and utilization of bridge amplification double-stranded molecules during each stage). Thus, this new method circumvents the problem of low amplification power of the original bridge amplification method by the implementation of a multi-stage bridge amplification procedure which employs a single-stranded amplification product to initiate a second stage of bridge amplification.

The features and other details of the invention will now be more particularly described and pointed out in the exemplification. It will be understood that the particular embodiments of the invention are shown by way of illustration and not as limitations of the invention. The principle features of this method are employed in various embodiments without departing from the scope of the invention.

Exemplification

Multi-Stage Bridge Amplification: Comparing the Use of Double-Stranded Versus Single-Stranded Amplification Nucleic Acid Molecules This example illustrates a two stage bridge amplification method using a yeast gene fragment (LEU2). The nucleotide sequence of yeast LEU2 gene, bases 7685 to 7943 (Genbank Accession No. AFO49063) is shown in FIG. 4. The oligonucleotide primers were synthesized with a 5'-acrylamide modification (Acrydite™ phosphoramidite, Mosaic Technologies, Boston, Mass.) which allows the primers to be immobilized to a solid support. In this case, the solid support is a polyacrylamide bead. Copolymerization of the modified primers with the acrylamide gel mix during bead fabrication produced a solid support with immobilized primers. The primers remained attached via the 5'-acrylamide groups during thermocycling. (Rehman et al., *Nucleic Acid Res.*, 27:649–655 (1999)).

Acrylamide beads with immobilized primers were prepared by pipetting 1 $\mu$L drops of a solution containing 10% polyacrylamide (acrylamide/bis, 29:1), 10 mM sodium borate buffer (pH 8.0), 100 $\mu$M of each 5'-acrylamide primer (Leu2F2.Pst: 5'-QTT TTT TTT TCT GCA GAA CCG TGG CAT GGT TC-3' [SEQ ID No. 1], and Leu2R3.Xho: 5'QTT TTT TTT TCT CGA GCT GTG GAG GAA ACC ATC AAG-3' [SEQ ID No. 2], restriction sites are italicized, "Q" represents a 5'-acrylamide group, and 0.2% ammonium persulfate (wt/vol) into degassed mineral oil containing 0.4% N,N,N',N'-tetramethylethylenediamine (TEMED). Amplification was allowed to proceed for thirty minutes at room temperature. Excess mineral oil was decanted and the beads were transferred to a 50 mL disposable tube containing 30 mL of TE buffer (10 mM Tris-HCl (pH 8.0) and 1 mM EDTA). The remaining mineral oil was extracted 2 to 3 times using chloroform (15 mL per extraction). The beads were then washed with several rounds of TE buffer (15 mL per round). To remove non-immobilized primers from the beads, the preparation was equilibrated with 0.5×TBE (89 mM Tris-borate (pH 8.3) and 2 mM EDTA) and placed into the wells of a vertical polyacrylamide gel, subsequently the preparation was subjected to electrophoresis for sixty minutes at 20 V/cm.

Prior to hybridization the beads were subjected to 15 thermocycles in the absence of DNA Polymerase to remove primers that were not thermally stable. The beads were then equilibrated for 1 to 2 hours with 1×thermopol buffer (10 mM KCl, 20 mM Tris-HCl (pH 8.8), 10 mM $(NH_4)_2SO_4$, 2 mM MgSO$_4$, 0.1% Triton X-100, New England Biolabs, Beverly, Mass.), plus 50 μg/mL bovine serum albumin (BSA) and 120 ng/mL denatured *E. coli* genomic DNA. Thermocycling was performed using a profile of thirty seconds each at 94° C., 60° C. and 72° C.

Hybridization and amplification were performed in separate steps. Each amplification reaction utilized a single 1 μL bead support. The yeast (*Saccharomyces cerevisiae*) target DNA was restricted using two restriction endonucleases that do not cut within the desired amplification target nucleic acid sequence (Sau96 and HincII, New England Biolabs, Beverly, Mass.). Hybridization reactions contained 1 primer-modified bead, 1×thermopol buffer, 50 μg/mL BSA and 50 μg/mL restricted yeast DNA in a total reaction volume of 100 μL. Reactions were initiated by a two minute denaturation at 94° C., and hybridization was carried out for thirty minutes at 60° C. in a shaking microplate incubator (Taitec Microincubator M-36, Taitec Instruments, San Jose, Calif.). After hybridization, the beads were washed once in 100 μL of 1×thermopol buffer with 50 μg/mL BSA at 60° C. with shaking for 10 minutes.

Following hybridization, the beads were transferred to a 30 μL amplification reaction mixture containing 1×thermopol buffer, 50 μg/mL BSA, 200 μM each dATP, dCTP, dGTP and dTTP, and 0.01 U/μL Vent DNA Polymerase (New England Biolabs, Beverly, Mass.). The reactions were incubated at 72° C. for five minutes to extend hybridized target molecules. After the initial extension, target molecules bound to the beads were amplified through 35 thermocycles consisting of thirty seconds each at 94° C., 60° C. and 72° C.

Following amplification, the beads were rinsed once using 1×NEB buffer 3 (50 mM Tris-HCl (pH 7.9 at 25° C.), 10 mM MgCl$_2$, 1 mM DTT) containing 0.1 mg/mL BSA. Products were then restricted from the beads using XhoI and PstI in combination, or PstI alone. Restriction reactions were performed in a 30 μL volume containing 1×NEB buffer 3, 0.1 mg/mL BSA, and 30 U of each restriction endonuclease (New England Biolabs, Beverly, Mass.). The restriction endonucleases XhoI and PstI cut within the 5'-terminal nucleotide sequences of the oligonucleotide primers. The restriction was performed for three hours at 37° C.

Following restriction digestion of the first stage, 10 μL of the doubly-restricted product were used as the input target nucleic acid molecule for the next stage of bridge amplification. A singly-restricted product was eluted from the PstI treated beads by heating at 94° C. for two minutes. Ten μL of the eluted product were used as the input target nucleic acid molecule for the second stage bridge amplifications.

The next stage (in this case, the second stage) hybridization and amplification were performed as that previously described above for the first stage. Products were restricted from the second stage solid supports with RsaI and EcoRI using the same buffer and method described for cleavage of the first stage amplification double-stranded nucleic acid molecules. RsaI and EcoRI cleaved within the double-stranded amplification products. Ten μL aliquots of each reaction were subjected to electrophoresis in a non-denaturing 1×TBE, 10% polyacrylamide gel (Novex, San Diego, Calif.). The gel was stained with SYBR green I (Molecular Probes, Eugene, Oreg.) and imaged using a Molecular Dynamics Fluorimager 595 (Molecular Dynamics, Sunnyvale, Calif.). (See FIG. 5).

Figure 5:
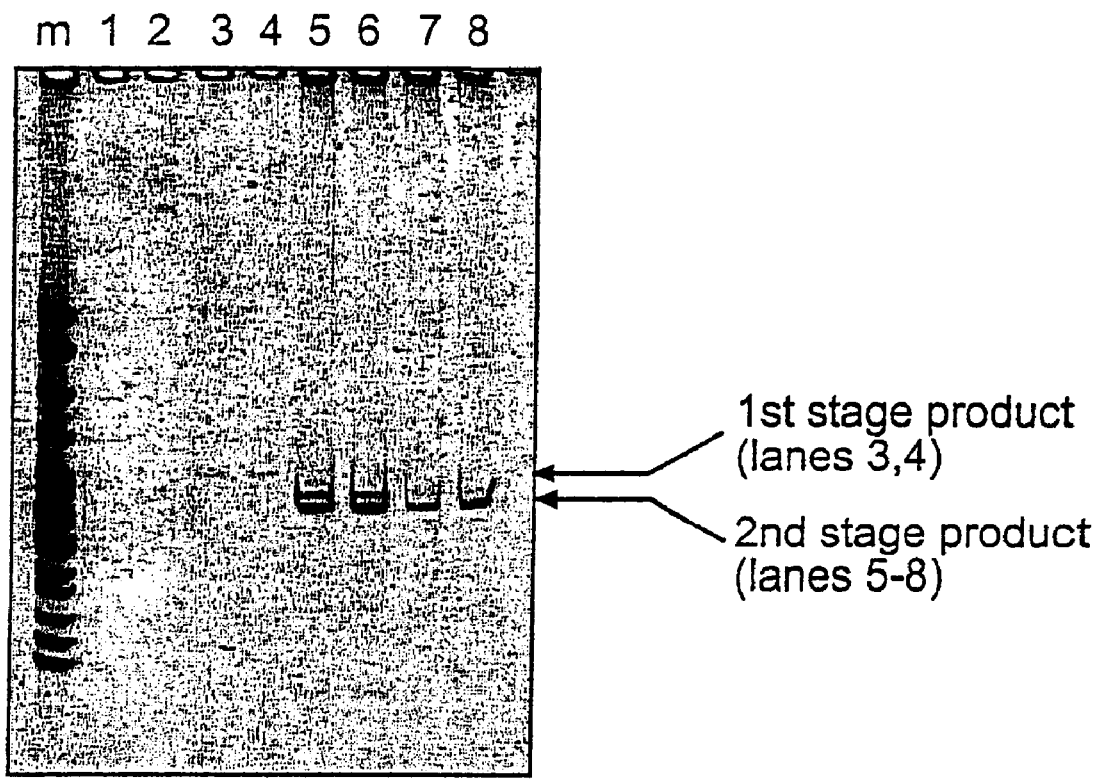
FIG. 5 is a photograph of a gel obtained from performing a two stage bridge amplification reaction comparing the use of a single-stranded target nucleic acid versus a double-stranded nucleic acid molecule as the DNA template for bridge amplification.

FIG. 5 illustrates the gel that was obtained from performing the experiment. Each of the lanes 3 through 6 were loaded with the double-stranded amplification products obtained from a single stage bridge amplification reaction. In each case, 10 μL, or 33% of a total 30 μL restriction reaction were loaded. The products shown in lanes 3 and 4 were from PstI-XhoI double digestion of a first stage amplification reaction. Lanes 5 and 6 show products from second stage reactions in which single-stranded first stage amplification products were used as the target nucleic acid input molecule for the second stage. Lanes 7 and 8 show products from second stage amplification reactions in which double-stranded first stage amplification products were used as target nucleic acid input molecules for the second stage. Lane "m" contains DNA size markers: 0.05 μg of an MspI digest of pBR322 (New England Biolabs, Beverly, Mass.).

Fluorimetric analysis of the products shown in lanes 5 through 8 demonstrate that when the first stage amplification products are added in single-stranded form, the second stage bridge amplification reaction produced significantly more product. The second stage products shown in lanes 7 and 8 show a 15-fold increase over the level of the first stage bridge amplification double-stranded nucleic acid molecule (lanes 3 and 4). In contrast, the amplification double-stranded nucleic acid molecules shown in lanes 5 and 6 show a 45-fold increase over the first stage product level. Thus, the use of single-stranded first stage product in the second bridge amplification stage improves the overall extent of amplification by approximately 3-fold in this experiment.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A solid-phase, multi-stage method of amplifying one, or more, target nucleic acid molecules comprising two or more stages of bridge amplification, wherein single-stranded amplification molecules produced in the first stage of bridge amplification initiate a second stage of bridge amplification, and each subsequent stage of bridge amplification is initiated with single-stranded amplification molecules produced in the previous stage of bridge amplification, wherein each stage of bridge amplification comprises the steps of:

(a) hybridizing target nucleic acid molecules to a set of oligonucleotide primers immobilized on a solid support;

(b) thermocycling to amplify the target nucleic acid molecules hybridized to the oligonucleotide primers by the formation of bridge amplification double-stranded molecules;

(c) cleaving and denaturing the bridge amplification double-stranded molecules to form single-stranded amplification molecules;

(d) recovering the single-stranded amplification molecules of step (c);

(e) contacting the single-stranded amplification molecules with a fresh solid support; and (f) repeating steps (a) through (e) to amplify the target nucleic acid molecules.

2. A method of amplifying one, or more, target nucleic acid molecules using a solid support comprising two or more immobilized oligonucleotide primers, of which at least one primer specifically hybridizes to the target nucleic acid molecules, comprising the steps of:

(a) hybridizing target nucleic acid molecules to a set of oligonucleotide primers immobilized on a solid support;

(b) thermocycling to amplify the target nucleic acid molecules hybridized to the oligonucleotide primers forming a double-stranded amplification molecule;

(c) cleaving and denaturing the double-stranded amplification molecule to form single-stranded amplification molecules;

(d) recovering the single-stranded amplification molecules of step (c), (e) contacting the single-stranded amplification molecules with a fresh solid support, and (f) repeating steps (a) through (e) to amplify the target nucleic acid molecules.

3. The method of claim 2, wherein the thermocycling step (b) comprises about 5 to about 50 thermocycles.

4. The method of claim 3, wherein each thermocycle comprises from about five seconds to about one minute each at 95° C., 60° C. and 72° C.

5. A method of amplifying one, or more, target nucleic acid molecules using a solid support comprising two or more immobilized oligonucleotide primers, of which at least one specifically hybridizes to the target nucleic acid molecule, comprising the steps of:

(a) forming a hybridization complex comprising a single-stranded target nucleic acid molecule hybridized to a first oligonucleotide primer immobilized to the solid support by contacting the target nucleic acid molecule with the solid support, under conditions suitable for hybridization;

(b) forming a first double-stranded amplification molecule comprising the target nucleic acid molecule hybridized to a first single-stranded amplification molecule by contacting the hybridization complex of step (a) with amplification reagents under conditions suitable for a primer-mediated polymerase extension reaction, wherein a first single-stranded amplification molecule is formed by extending the first primer with deoxynucleotides to form a complementary strand to the target nucleic acid molecule;

(c) denaturing the first double-stranded amplification molecule of (b), thereby releasing the single-stranded target molecule from the first double-stranded amplification molecule;

(d) forming a first bridge hybridization complex comprising the first single-stranded amplification molecule of step (b) and a second oligonucleotide primer immobilized to the solid support, under conditions suitable for hybridization;

(e) forming a second double-stranded amplification molecule by contacting the bridge hybridization complex of step (d) with amplification reagents, under conditions suitable for a primer-mediated amplification reaction, wherein a second single-stranded amplification molecule is formed that is complementary to and base-paired with the first single-stranded amplification molecule of step (d);

(f) denaturing the second double-stranded amplification molecule of (e) to produce first and second single-stranded amplification molecules immobilized to the solid support;

(g) forming second bridge hybridization complexes comprising
  (i) the first single-stranded amplification molecule of step (f) and a second oligonucleotide primer immobilized to the solid support, under conditions suitable for hybridization, and
  (ii) the second single-stranded amplification molecule of step (f) and a first oligonucleotide primer immobilized to the solid support, under conditions suitable for hybridization;

(h) forming a third and fourth double-stranded amplification molecule by contacting the second bridge hybridization complexes of step (g) with amplification reagents, under conditions suitable for a primer-mediated amplification reaction, wherein
  (i) the third double-stranded amplification molecule comprises a nascent third single-stranded amplification molecule that is complementary to and is base-paired with the first single-stranded amplification molecule, and
  (ii) the fourth double-stranded amplification molecule comprises a nascent fourth single-stranded amplification molecule that is complementary to and is base-paired with the second single-stranded amplification molecule;

(i) cleaving one, or more, first oligonucleotide primers, thereby cleaving the third and fourth double-stranded amplification molecules from at least one attachment to the solid support, or alternatively cleaving one, or more, second oligonucleotide primers, thereby cleaving the third and fourth double-stranded amplification molecules from at least one attachment to the solid support;

(j) denaturing the cleaved amplification double-stranded molecules of (h), thereby releasing amplification single-stranded molecules from the solid support;

(k) applying released single-stranded molecules from step (j) to fresh solid supports comprising unused immobilized oligonucleotide primers, and (l) repeating steps (a) through (k) one, or more, times, thereby amplifying the target nucleic acid molecules.

6. The method of claim 5, wherein steps (f), (g) and (h) are repeated from about 5 to about 50 times.

7. The method of claim 5, wherein the oligonucleotide primers are immobilized to the solid support through one, or more, covalent interactions.

8. The method of claim 7, wherein the oligonucleotide primers are immobilized via co-polymerization with a polymeric surface layer on the solid support.

9. The method of claim 5 wherein in step (i), the oligonucleotide primers are cleaved using chemical means.

10. The method of claim 9, wherein the chemical means is selected from reagents that reduce disulfide bonds.

11. The method of claim 10, wherein the reducing reagents are selected from the group consisting of: DTT, β-mercaptoethanol and TCEP.

12. The method of claim 5 wherein in step (i), the oligonucleotide primers are cleaved using photochemical means.

13. The method of claim 12, wherein the oligonucleotide primers comprise a nitrophenol moiety.

14. The method of claim 5 wherein in step (i), the oligonucleotide primers are cleaved using enzymatic means.

15. The method of claim 14, wherein the enzymatic means is accomplished using one, or more, restriction endonucleases.

16. The method of claim 5, wherein the denaturant used for denaturing the double-stranded amplification molecules is denatured using at least one of the following denaturants selected from the group consisting of: high temperature, high pH, organic solvent, chaotropic agent and combinations thereof.

17. The method of claim 5, wherein the material composition of the solid support is selected from the group consisting of: plastic, glass, silica, nylon, metal, metal alloys, polyacrylamide, polyacrylates, crosslinked-dextran and combinations thereof.

18. The method of claim 5, wherein the solid support is a bead.

19. The method of claim 18, wherein the bead comprises one, or more, oligonucleotide primer sets for more than one target nucleic acid molecule.

20. The method of claim 5, wherein the oligonucleotide primers are from about 5 to about 500 in nucleotide length.

21. The method of claim 5, wherein one or more amplification products are labeled.

22. The method of claim 21, wherein the label is selected from the group consisting of: radioactivity, chemiluminescence, luminescence and fluorescence.

23. A solid-phase, multi-stage method of detecting the presence or absence of one, or more target nucleic acid molecules comprising two or more stages of bridge amplification, wherein single-stranded amplification molecules produced in the first stage of bridge amplification initiate a second stage of bridge amplification, and each subsequent stage of bridge amplification is initiated with single-stranded amplification molecules produced in the previous stage of bridge amplification, wherein each stage of bridge amplification comprises the steps of:

(a) hybridizing target nucleic acid molecules to a set of oligonucleotide primers immobilized on a solid support;
  (b) thermocycling to amplify the target nucleic acid molecules hybridized to the oligonucleotide primers by the formation of bridge amplification double-stranded molecules;
  (c) cleaving and denaturing the bridge amplification double-stranded molecules to form single-stranded amplification molecules;
  (d) recovering the single-stranded amplification molecules of step (c), and
  (e) contacting the single-stranded amplification molecules with a fresh solid support;
  (f) repeating steps (a) through (e) to amplify the target nucleic acid molecules, and
  (g) detecting the presence of the target molecules, wherein the detection of the single-stranded or double-stranded amplification molecules is indicative of the target molecules in a test sample.

24. A method of detecting the presence or absence of one, or more, target nucleic acid molecules using a solid support comprising two or more immobilized oligonucleotide primers, of which at least one primer specifically hybridizes to the target nucleic acid molecules, comprising the steps of:

(a) hybridizing target nucleic acid molecules to a set of oligonucleotide primers immobilized on a solid support;

(b) thermocycling to amplify the target nucleic acid molecules hybridized to the oligonucleotide primers forming a double-stranded amplification molecule;

(c) cleaving and denaturing the double-stranded amplification molecule to form single-stranded amplification molecules;

(d) recovering the single-stranded amplification molecules of step (c), (e) contacting the single-stranded amplification molecules with a fresh solid support, and (f) repeating steps (a) through (e) to amplify the target nucleic acid molecules, and (g) detecting the presence of the target molecules, wherein the detection of the single-stranded or double-stranded amplification molecules is indicative of the target molecules in a test sample.

25. The method of claim 24, wherein the thermocycling step (b) comprises about 5 to about 50 thermocycles.

26. The method of claim 25, wherein each thermocycle comprises about one minute each at 95° C., 60° C. and 72° C.

27. The method of claim 24, wherein one or more single-stranded amplification molecules are labeled.

28. The method of claim 27, wherein the label is selected from the group consisting of: radioactivity, chemiluminescence, luminescence and fluorescence.

29. The method of claim 1 wherein the thermocycling step (b) comprises about 5 to about 50 thermocycles.

30. The method of claim 23 wherein the one or more of the single-stranded amplification molecules are labeled.

31. The method of claim 30 wherein the label is selected from the group consisting of: radioactive labels, chemiluminescent labels, luminescent labels and fluorescent labels.

32. The method of claim 23 wherein the thermocycling step (b) comprises about 5 to about 5 thermocycles.

* * * * *

UNITED STATES PATENT AND TRADEMARK OFFICE
Certificate

Patent No. 6,300,070 B1

Patented: October 9, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: T. Christian Boles, Waltham, MA; Ezra S. Abrams, West Newton, MA; Christopher P. Adams, Somerville, MA: Thomas R. Gingeras, Encinitas, CA; and Stephen P. A. Fodor, Palo Alto, CA.

Signed and Sealed this Fourth Day of January 2005.

W. GARY JONES
*Supervisory Patent Examiner*
Art Unit 1634